United States Patent
Chen et al.

(10) Patent No.: US 12,128,097 B2
(45) Date of Patent: Oct. 29, 2024

(54) AD35-VECTORED IMMUNOGENIC COMPOSITION FOR SARS-COV-2 INFECTION

(71) Applicant: GUANGZHOU N BIOMED LTD., Guangzhou (CN)

(72) Inventors: Ling Chen, Guangzhou (CN); Suhua Guan, Guangzhou (CN); Chenchen Yang, Guangzhou (CN); Qian Wang, Guangzhou (CN)

(73) Assignee: GUANGZHOU N BIOMED LTD., Guangzhou (CN)

( * ) Notice: Subject to any disclaimer, the term of this patent is extended or adjusted under 35 U.S.C. 154(b) by 658 days.

(21) Appl. No.: 17/598,624

(22) PCT Filed: Feb. 2, 2021

(86) PCT No.: PCT/CN2021/074838
§ 371 (c)(1),
(2) Date: Sep. 27, 2021

(87) PCT Pub. No.: WO2021/184988
PCT Pub. Date: Sep. 23, 2021

(65) Prior Publication Data
US 2022/0331420 A1    Oct. 20, 2022

(30) Foreign Application Priority Data

Mar. 16, 2020  (CN) .......................... 202010182106.3
Apr. 15, 2020  (CN) .......................... 202010293659.6
Sep. 27, 2020  (CN) .......................... 202011030466.8

(51) Int. Cl.
*A61K 39/215*  (2006.01)
*A61K 39/00*   (2006.01)
*A61K 45/06*   (2006.01)
*A61P 31/14*   (2006.01)

(52) U.S. Cl.
CPC ............ *A61K 39/215* (2013.01); *A61K 45/06* (2013.01); *A61P 31/14* (2018.01); *A61K 2039/5254* (2013.01); *A61K 2039/5256* (2013.01)

(58) Field of Classification Search
CPC ................. A61K 39/215; A61K 45/06; A61K 2039/5254; A61K 2039/5256; A61K 2039/53; A61K 39/12; A61P 31/14; A61P 11/00; C12N 2710/10343; C12N 2770/20034
See application file for complete search history.

(56) References Cited

FOREIGN PATENT DOCUMENTS

| | | |
|---|---|---|
| CN | 1562365 A | 1/2005 |
| CN | 110951756 A | 4/2020 |
| CN | 110974950 A | 10/2020 |
| CN | 112220918 A | 1/2021 |
| WO | 2004110483 A1 | 12/2004 |

OTHER PUBLICATIONS

Kim, MH et al. Superior immune responses induced by intranasal immunization with recombinant adenovirus-based vaccine expressing full-length Spike protein of Middle East respiratory syndrome coronavirus PLOS ONE Jul. 22, 2019 (Jul. 22, 2019) Issue 7 vol. 14.

*Primary Examiner* — Nicole Kinsey White
*Assistant Examiner* — Samadhan Jaising Jadhao
(74) *Attorney, Agent, or Firm* — D'Ambrosio & Menon, PLLC; Usha Menon (57) ABSTRACT

Disclosed is a replication-defective Ad35-vectored immunogenic composition for inducing immune response against SARS COV-2, comprising an Ad35 vector, wherein the Ad35 vector encodes the optimized nucleic acid sequence of SEQ ID NO: 1. Some embodiments of the present disclosure have better safety and use convenience. Experiments have shown that the immunogenic composition can produce more S proteins in human cells. Some embodiments of the present disclosure may be used in combination with another immunogenic composition or may also be used as a therapeutic immunogenic composition for Corona Virus Disease 2019. When a patient is immunized with the Ad35-vectored immunogenic composition of the present disclosure at the initial stage of infection, the immunogenic composition induces an immune response in the human body, thereby achieving a therapeutic effect.

19 Claims, 2 Drawing Sheets
Specification includes a Sequence Listing.

1. pGA351-NB2  2. pGA351-NB1  3. MARKER  4. Ad35-NB2  5. Ad35 empty vector

FIG. 3

SEQUENCE LISTING

<160> NUMBER OF SEQ ID NOS: 7

<210> SEQ ID NO 1
<211> LENGTH: 3822
<212> TYPE: DNA

<213> ORGANISM: Artificial Sequence
<220> FEATURE:
<223> OTHER INFORMATION: synthesized

<400> SEQUENCE: 1

```
atgttcgtgt ttctggtgct gctgcctctg gtgagctccc agtgcgtgaa cctgaccaca      60
aggacccagc tgccacctgc ctataccaat agcttcacac ggggcgtgta ctatcccgac     120
aaggtgttta gatctagcgt gctgcactcc acccaggatc tgtttctgcc tttcttttct     180
aacgtgacat ggttccacgc catccacgtg tccggcacca atggcacaaa gcggttcgac     240
aatccagtgc tgcccttttaa cgatggcgtg tacttcgcct ccaccgagaa gtctaacatc     300
atcagaggct ggatctttgg caccacactg gacagcaaga cccagtccct gctgatcgtg     360
aacaatgcca caaacgtggt catcaaggtg tgcgagttcc agttttgtaa tgatcccttc     420
ctgggcgtgt actatcacaa gaacaataag tcttggatgg gagcgagtt tagggtgtat     480
tcctctgcca caattgcac ctttgagtac gtgagccagc cttcctgat ggacctggag     540
ggcaagcagg gcaatttcaa gaacctgagg gagttcgtgt taagaatat cgatggctac     600
ttcaagatct actccaagca cacaccaatc aacctggtgc gcgacctgcc acagggcttc     660
tctgccctgg agccactggt ggatctgccc atcggcatca acatcacccg gtttcagaca     720
ctgctggccc tgcacagaag ctacctgacc ccaggcgaca gctcctctgg atggacagca     780
ggagctgccg cctactatgt gggctatctg cagccccgca ccttcctgct gaagtacaac     840
gagaatggca ccatcacaga cgcagtggat tgcgccctgg accccctgtc tgagaccaag     900
tgtacactga gagctttac agtggagaag ggcatctacc agaccagcaa cttcagggtg     960
cagccaacag agtccatcgt gcgctttccc aatatcacca acctgtgccc ttttggcgag    1020
gtgttcaatg ccacacgctt cgccagcgtg tacgcctgga ataggaagcg catctccaac    1080
tgcgtggccg actattctgt gctgtacaac agcgcctcct tctctacctt taagtgttat    1140
ggcgtgagcc ccaccaagct gaatgatctg tgctttacaa acgtgtacgc cgattccttc    1200
gtgatcaggg gcgacgaggt gcgccagatc gcaccaggac agaccggcaa gatcgcagac    1260
tacaattata gctgcctga cgatttcaca ggctgcgtga tcgcctggaa ctctaacaat    1320
ctggatagca aagtgggcgg caactacaat tatctgtacc ggctgttag aaagtctaat    1380
ctgaagccat cgagcggga catctccacc gagatctacc aggccggctc tacaccctgc    1440
aatggcgtgg agggctttaa ctgttatttc cctctgcagt cctacggctt ccagccaacc    1500
aacggcgtgg gctatcagcc ctacagagtg gtggtgctgt cttttgagct gctgcacgca    1560
cctgcaaccg tgtgcggccc aaagaagagc acaaatctgg tgaagaacaa gtgcgtgaac    1620
ttcaacttca cggactgac cggcacaggc gtgctgaccg agagcaacaa gaagttcctg    1680
ccatttcagc agttcggcag ggacatcgca gataccacag acgccgtgcg cgaccctcag    1740
accctggaga tcctggacat cacaccatgt tccttcggcg cgtgtctgt gatcaccca    1800
ggcaccaata catccaacca ggtggccgtg ctgtatcagg acgtgaattg cacagaggtg    1860
cccgtggcaa tccacgcaga tcagctgacc cctacatggc gggtgtactc taccggcagc    1920
aacgtgttcc agacaagagc cggatgcctg atcgagcag agcacgtgaa caatagctat    1980
gagtgcgaca tccctatcgg cgccggcatc tgtgcctcct accagaccca gacaaactcc    2040
ccaaggagag cccggtctgt ggccagccag tccatcatcg cctataccat gagcctgggc    2100
gccgagaaca gcgtggccta ctccaacaat tctatcgcca tccctaccaa cttcacaatc    2160
agcgtgacca cagagatcct gccagtgagc atgaccaaga catccgtgga ctgcaccatg    2220
```

-continued

| | |
|---|---|
| tatatctgtg gcgattccac agagtgttct aacctgctgc tgcagtacgg ctccttttgc | 2280 |
| acccagctga atagagccct gacaggcatc gccgtggagc aggacaagaa cacccaggag | 2340 |
| gtgttcgccc aggtgaagca gatctacaag acaccaccca tcaaggactt tggcggcttc | 2400 |
| aacttcagcc agatcctgcc cgatcctagc aagccatcca gcggtctttt atcgaggac | 2460 |
| ctgctgttca acaaggtgac cctggccgat gccggcttca tcaagcagta tggcgattgt | 2520 |
| ctgggcgaca tcgccgccag agacctgatc tgcgcccaga gtttaatgg cctgaccgtg | 2580 |
| ctgcctccac tgctgacaga tgagatgatc gcacagtaca cctctgccct gctggccggc | 2640 |
| accatcacaa gcggatggac attcggcgca ggagccgccc tgcagatccc ctttgccatg | 2700 |
| cagatggcct atcggttcaa cggcatcggc gtgacccaga atgtgctgta cgagaaccag | 2760 |
| aagctgatcg ccaatcagtt taacagcgcc atcggcaaga tccaggactc tctgagctcc | 2820 |
| accgccagcg ccctgggcaa gctgcaggat gtggtgaatc agaacgccca ggccctgaat | 2880 |
| acactggtga agcagctgtc tagcaacttc ggcgccatct cctctgtgct gaatgacatc | 2940 |
| ctgagccggc tggacaaggt ggaggcagag gtgcagatcg accggctgat caccggcaga | 3000 |
| ctgcagtccc tgcagaccta cgtgacacag cagctgatca gggcagcaga gatcagggcc | 3060 |
| tctgccaatc tggccgccac aaagatgagc gagtgcgtgc tgggacagtc caagagggtg | 3120 |
| gacttttgcg gcaagggcta tcacctgatg agcttccac agtccgcccc tcacggagtg | 3180 |
| gtgtttctgc acgtgaccta cgtgccagcc caggagaaga acttcaccac agccccgcc | 3240 |
| atctgtcacg atggcaaggc ccactttcct agggagggcg tgttcgtgag caacggcacc | 3300 |
| cactggtttg tgacacagcg caatttctac gagccacaga tcatcaccac agacaatacc | 3360 |
| ttcgtgtccg gcaactgcga cgtggtcatc ggcatcgtga acaatacagt gtatgatcct | 3420 |
| ctgcagccag agctggactc ttttaaggag gagctggata agtacttcaa gaatcacacc | 3480 |
| agccccgacg tggatctggg cgacatctct ggcatcaatg ccagcgtggt gaacatccag | 3540 |
| aaggagatcg acagactgaa cgaggtggcc aagaatctga cgagagcct gatcgatctg | 3600 |
| caggagctgg gcaagtatga gcagtacatc aagtggcct ggtatatctg gctgggcttc | 3660 |
| atcgccggcc tgatcgccat cgtgatggtg accatcatgc tgtgctgtat gacaagctgc | 3720 |
| tgttcctgcc tgaagggctg ctgttcttgt ggcagctgct gtaagtttga tgaggacgat | 3780 |
| tccgagcctg tgctgaaggg cgtgaagctg cactacacct aa | 3822 |

<210> SEQ ID NO 2
<211> LENGTH: 59
<212> TYPE: DNA
<213> ORGANISM: Artificial Sequence
<220> FEATURE:
<223> OTHER INFORMATION: synthesized

<400> SEQUENCE: 2

| | |
|---|---|
| gcgtttaaac ttaagcttgg taccgagctc ggatccgcca ccatgtttgt ttttcttgt | 59 |

<210> SEQ ID NO 3
<211> LENGTH: 42
<212> TYPE: DNA
<213> ORGANISM: Artificial Sequence
<220> FEATURE:
<223> OTHER INFORMATION: synthesized

<400> SEQUENCE: 3

| | |
|---|---|
| agaatagggc cctctagact agtttatgtg taatgtaatt tg | 42 |

```
<210> SEQ ID NO 4
<211> LENGTH: 59
<212> TYPE: DNA
<213> ORGANISM: Artificial Sequence
<220> FEATURE:
<223> OTHER INFORMATION: synthesized

<400> SEQUENCE: 4
gcgtttaaac ttaagcttgg taccgagctc ggatccgcca ccatgttcgt gtttctggt       59

<210> SEQ ID NO 5
<211> LENGTH: 45
<212> TYPE: DNA
<213> ORGANISM: Artificial Sequence
<220> FEATURE:
<223> OTHER INFORMATION: synthesized

<400> SEQUENCE: 5
agaatagggc cctctagact agtttatcag gtgtagtgca gcttc                     45

<210> SEQ ID NO 6
<211> LENGTH: 26
<212> TYPE: DNA
<213> ORGANISM: Artificial Sequence
<220> FEATURE:
<223> OTHER INFORMATION: synthesized

<400> SEQUENCE: 6
tctagagggc cctattctat agtgtc                                          26

<210> SEQ ID NO 7
<211> LENGTH: 46
<212> TYPE: DNA
<213> ORGANISM: Artificial Sequence
<220> FEATURE:
<223> OTHER INFORMATION: synthesized

<400> SEQUENCE: 7
ggatccgagc tcggtaccaa gcttaagttt aaacgctaga gtccgg                    46
```

AD35-VECTORED IMMUNOGENIC COMPOSITION FOR SARS-COV-2 INFECTION

CROSS-REFERENCE TO RELATED APPLICATIONS

The present application is a national phase entry under 35 USC § 371 of International Application PCT/CN2021/074838, filed on Feb. 2, 2021, which claims the benefit of and priority to Chinese Patent Application No. 2020101821063, No.2020102936596 and No.2020110304668, filed on Mar. 16, 2020, Apr. 15, 2020 and Sep. 27, 2020 respectively, the entire disclosures of which are incorporated herein by reference.

INCORPORATION BY REFERENCE

This application includes a sequence listing in computer readable form (a "txt" file) that is submitted herewith on an ASCII text file named Sequence_listing.txt, created on Apr. 12, 2022 and 6,401 bytes in size. This sequence listing is incorporated by reference herein.

FIELD OF THE INVENTION

The present disclosure relates to an Ad35-vectored vaccine for preventing SARS-CoV-2 infection.

BACKGROUND OF THE INVENTION

The Corona Virus Disease 2019 (COVID-19) is very severe and has spread in many countries around the world. As of Mar. 6, 2020, there have been more than 100,000 confirmed cases of the Corona Virus Disease 2019 around the world. However, there have been currently no clearly verified specific antiviral drugs and preventive vaccines against the SARS-CoV-2 at home and abroad. Therefore, preventing and blocking the spread of the virus is the key to controlling the Corona Virus Disease 2019. Vaccines are the most economical and effective intervention measure to prevent and control SARS-CoV-2 infection. The published results obtained from the alignment of more than one hundred SARS-CoV-2 virus genomes have shown that the overall degree of mutation of the virus is relatively low, and no recombination phenomenon has been found. Therefore, SARS-CoV-2 vaccines, if successfully developed, will necessarily be able to protect the human population from infection with SARS-CoV-2, thereby suppressing the outbreak of a new epidemic.

In the virus particle structure of SARS-CoV-2, S protein that constitutes a "crown" is an obvious target, which has become the focus studied by most research teams. The complete sequence of SARS-CoV-2 is as shown in NC_045512.2, in which the 21563 to 25384 nucleic acid is a coding sequence of Spike protein (S), wherein the full length of the S protein is 1273 aa. Through computer simulation of the three-dimensional structure of the S protein, existing research teams have successfully revealed the relationship between the S protein and an ACE2 receptor during its invasion of cells. The S protein plays an important role in mediating the binding of a virus particle to a host cell receptor and inducing a neutralizing antibody. Therefore, vaccines with the S protein as an antigen, including nucleic acid vaccines, subunit vaccines and virus-vectored vaccines, are very promising to prevent SARS-CoV-2 infection; however, the expression levels and protein structures of the S proteins in these vaccines determine the efficacies of such vaccines.

However, experiments have shown that the expression level of the S gene of the Spike protein of natural SARS-CoV-2 in human kidney cells HEK293 is very low, and therefore, if the original S codons are used for expression as an antigen, the vaccine would be ineffective or have a low titer, which is not enough to resist the viral infection.

Adenoviruses are common vectors in vaccine development and gene therapies, and have been widely used in the field of biomedicine. Compared with other viral vectors, adenoviruses have a low toxicity, and infection with adenoviruses only causes mild cold symptoms. At present, most adenovirus-vectored vaccines developed by research teams are based on adenovirus type 5. Preformed antibodies against adenovirus type 5 vectors have a very high proportion in the human population, which will affect the titer of adenovirus type 5 vectored vaccines to a certain extent.

SUMMARY OF THE INVENTION

An object of the present disclosure is to provide an Ad35-vectored vaccine for preventing SARS-CoV-2 infection, in order to overcome at least one deficiency of the prior art.

The present disclosure blocks SARS-CoV-2 infection by integrating an optimized S gene onto a replication-defective Ad35 vector, infecting cells via an adenovirus, presenting an antigen against SARS-CoV-2, and producing a specific immune response in an organism after immunization. The proportion of preformed antibodies against Ad35 in the human population is lower than the proportion of those against Ad5, and therefore, the Ad35 vector can be prevented from being neutralized by the preformed antibodies in the human body, such that the immune effect of an Ad35-vectored vaccine is expected to be higher than that of an Ad5-vectored vaccine. In addition, the replication capability of Ad35 is higher than that of Ad5, and in terms of vaccine production, the cost of the Ad35-vectored vaccine is expected to be lower than that of an Ad5-vectored vaccine.

The technical solution adopted by the present disclosure is:
an Ad35-vectored vaccine for preventing SARS-CoV-2 infection, comprising an Ad35 vector, wherein the Ad35 vector is loaded with a nucleic acid sequence shown in SEQ ID NO: 1.

In some embodiments, the Ad35 vector is a replication-defective Ad35 vector.

In some embodiments, the replication-defective Ad35 vector is a replication-defective Ad35 vector with genes in E1 and E3 regions deleted.

By using the replication-defective Ad35 vector, the replication of the Ad35 vector in cells can be effectively avoided, thereby improving the safety of the product.

In some embodiments, the transcription direction of the nucleic acid sequence shown in SEQ ID NO: 1 is opposite to the transcription direction of the other genes of the Ad35 vector. In this way, the nucleic acid sequence shown in SEQ ID NO: 1 can be better expressed, which is beneficial to improve the safety and titer of the product.

In this way, the vector can more exclusively express the nucleic acid sequence shown in SEQ ID NO: 1, thereby increasing the titer of the vaccine while improving the safety.

In some embodiments, the Ad35 vector has an element for regulating the expression of the nucleic acid sequence shown in SEQ ID NO: 1. In this way, the expression of the nucleic acid sequence shown in SEQ ID NO: 1 can be more artificially regulated to obtain better safety.

In some embodiments, the nucleic acid sequence can be expressed as a protein in a human-derived cell or the human body.

In some embodiments, the protein is capable of, in the human body:
inducing an immune response; or
generating a biological reporter molecule; or
generating a trace molecule for detection; or
regulating a gene function; or
acting as a therapeutic molecule.

In some embodiments, the Ad35-vectored vaccine further comprises at least one selected form the group consisting of pharmaceutically acceptable adjuvant, carrier, diluent or excipient. The adjuvant, carrier, diluent or excipient can be accordingly selected according to the specific dosage form of the vaccine.

In some embodiments, the dosage form of the Ad35-vectored vaccine includes, but not limited to common vaccine dosage forms, such as an injection, an oral preparation, and an aerosol inhalant.

In some embodiments, the adenovirus-vectored vaccine may also be used in combination with another vaccine.

In some embodiments, the Ad35-vectored vaccine further comprises at least one drug that has a therapeutic effect on COVID-19.

The beneficial effects of the present disclosure are provided as below:

Some embodiments of the present disclosure have better safety and use convenience. Experiments have shown that the vaccine can produce more S proteins in human cells, which is expected to be developed as a vaccine for preventing SARS-CoV-2 infection.

Some embodiments of the present disclosure may be used in combination with another vaccine, or may also be used as a therapeutic vaccine for Corona Virus Disease 2019. When a patient is vaccinated with the Ad35-vectored vaccine of the present disclosure at the initial stage of infection, the vaccine quickly induces an immune response in the human body, thereby achieving a therapeutic effect.

DETAILED DESCRIPTION OF THE EMBODIMENTS

The amino acid sequence of Spike (S) protein of SARS-CoV-2 is shown in YP_009724390.1, with a full length of 1273 aa, denoted as NB1.

pre-mRNA transcribed by eukaryotic cells can produce various mRNA splicing isoforms by various splicing modes (by selecting different splicing site combinations), which ultimately leads to various proteins resulting from the same gene sequence. This is very unfavorable for the expression of the protein. By performing codon optimization on the wild-type natural nucleic acid sequence while removing potential variable splicing sites based on self-owned technology, the inventors ensured the uniqueness of the expression of the protein and reduced the difficulty in the subsequent purification of the protein. The optimized nucleic acid sequence is denoted as NB2, and the specific sequence thereof is shown in SEQ ID NO: 1:

```
(SEQ ID NO.: 1)
ATGTTCGTGTTTCTGGTGCTGCTGCCTCTGGTGAGCTCCCAGTGCGTGAA

CCTGACCACAAGGACCCAGCTGCCACCTGCCTATACCAATAGCTTCACAC

GGGGCGTGTACTATCCCGACAAGGTGTTTAGATCTAGCGTGCTGCACTCC

ACCCAGGATCTGTTTCTGCCTTTCTTTTCTAACGTGACATGGTTCCACGC

CATCCACGTGTCCGGCACCAATGGCACAAAGCGGTTCGACAATCCAGTGC

TGCCCTTTAACGATGGCGTGTACTTCGCCTCCACCGAGAAGTCTAACATC

ATCAGAGGCTGGATCTTTGGCACCACACTGGACAGCAAGACCCAGTCCCT

GCTGATCGTGAACAATGCCACAAACGTGGTCATCAAGGTGTGCGAGTTCC

AGTTTTGTAATGATCCCTTCCTGGGCGTGTACTATCACAAGAACAATAAG

TCTTGGATGGAGAGCGAGTTTAGGGTGTATTCCTCTGCCAACAATTGCAC

CTTTGAGTACGTGAGCCAGCCTTTCCTGATGGACCTGGAGGGCAAGCAGG

GCAATTTCAAGAACCTGAGGGAGTTCGTGTTTAAGAATATCGATGGCTAC

TTCAAGATCTACTCCAAGCACACACCAATCAACCTGGTGCGCGACCTGCC

ACAGGGCTTCTCTGCCCTGGAGCCACTGGTGGATCTGCCCATCGGCATCA

ACATCACCCGGTTTCAGACACTGCTGGCCCTGCACAGAAGCTACCTGACC

CCAGGCGACAGCTCCTCTGGATGGACAGCAGGAGCTGCCGCCTACTATGT

GGGCTATCTGCAGCCCCGCACCTTCCTGCTGAAGTACAACGAGAATGGCA

CCATCACAGACGCAGTGGATTGCGCCCTGGACCCCCTGTCTGAGACCAAG

TGTACACTGAAGAGCTTTACAGTGGAGAAGGGCATCTACCAGACCAGCAA

CTTCAGGGTGCAGCCAACAGAGTCCATCGTGCGCTTTCCCAATATCACCA

ACCTGTGCCCTTTTGGCGAGGTGTTCAATGCCACACGCTTCGCCAGCGTG

TACGCCTGGAATAGGAAGCGCATCTCCAACTGCGTGGCCGACTATTCTGT

GCTGTACAACAGCGCCTCCTTCTCTACCTTTAAGTGTTATGGCGTGAGCC

CCACCAAGCTGAATGATCTGTGCTTTACAAACGTGTACGCCGATTCCTTC

GTGATCAGGGGCGACGAGGTGCGCCAGATCGCACCAGGACAGACCGGCAA

GATCGCAGACTACAATTATAAGCTGCCTGACGATTTCACAGGCTGCGTGA

TCGCCTGGAACTCTAACAATCTGGATAGCAAAGTGGGCGGCAACTACAAT

TATCTGTACCGGCTGTTTAGAAAGTCTAATCTGAAGCCATTCGAGCGGGA

CATCTCCACCGAGATCTACCAGGCCGGCTCTACACCCTGCAATGGCGTGG

AGGGCTTTAACTGTTATTTCCCTCTGCAGTCCTACGGCTTCCAGCCAACC

AACGGCGTGGGCTATCAGCCCTACAGAGTGGTGGTGCTGTCTTTTGAGCT

GCTGCACGCACCTGCAACCGTGTGCGGCCCAAAGAAGAGCACAAATCTGG

TGAAGAACAAGTGCGTGAACTTCAACTTCAACGGACTGACCGGCACAGGC

GTGCTGACCGAGAGCAACAAGAAGTTCCTGCCATTTCAGCAGTTCGGCAG

GGACATCGCAGATACCACAGACGCCGTGCGCGACCCTCAGACCCTGGAGA

TCCTGGACATCACACCATGTTCCTTCGGCGGCGTGTCTGTGATCACCCCA
```

-continued

```
GGCACCAATACATCCAACCAGGTGGCCGTGCTGTATCAGGACGTGAATTG

CACAGAGGTGCCCGTGGCAATCCACGCAGATCAGCTGACCCCTACATGGC

GGGTGTACTCTACCGGCAGCAACGTGTTCCAGACAAGAGCCGGATGCCTG

ATCGGAGCAGAGCACGTGAACAATAGCTATGAGTGCGACATCCCTATCGG

CGCCGGCATCTGTGCCTCCTACCAGACCCAGACAAACTCCCCAAGGAGAG

CCCGGTCTGTGGCCAGCCAGTCCATCATCGCCTATACCATGAGCCTGGGC

GCCGAGAACAGCGTGGCCTACTCCAACAATTCTATCGCCATCCCTACCAA

CTTCACAATCAGCGTGACCACAGAGATCCTGCCAGTGAGCATGACCAAGA

CATCCGTGGACTGCACCATGTATATCTGTGGCGATTCCACAGAGTGTTCT

AACCTGCTGCTGCAGTACGGCTCCTTTTGCACCCAGCTGAATAGAGCCCT

GACAGGCATCGCCGTGGAGCAGGACAAGAACACCCAGGAGGTGTTCGCCC

AGGTGAAGCAGATCTACAAGACACCACCCATCAAGGACTTTGGCGGCTTC

AACTTCAGCCAGATCCTGCCCGATCCTAGCAAGCCATCCAAGCGGTCTTT

TATCGAGGACCTGCTGTTCAACAAGGTGACCCTGGCCGATGCCGGCTTCA

TCAAGCAGTATGGCGATTGTCTGGGCGACATCGCCGCCAGAGACCTGATC

TGCGCCCAGAAGTTTAATGGCCTGACCGTGCTGCCTCCACTGCTGACAGA

TGAGATGATCGCACAGTACACCTCTGCCCTGCTGGCCGGCACCATCACAA

GCGGATGGACATTCGGCGCAGGAGCCGCCCTGCAGATCCCCTTTGCCATG

CAGATGGCCTATCGGTTCAACGGCATCGGCGTGACCCAGAATGTGCTGTA

CGAGAACCAGAAGCTGATCGCCAATCAGTTTAACAGCGCCATCGGCAAGA

TCCAGGACTCTCTGAGCTCCACCGCCAGCGCCCTGGGCAAGCTGCAGGAT

GTGGTGAATCAGAACGCCCAGGCCCTGAATACACTGGTGAAGCAGCTGTC

TAGCAACTTCGGCGCCATCTCCTCTGTGCTGAATGACATCCTGAGCCGGC

TGGACAAGGTGGAGGCAGAGGTGCAGATCGACCGGCTGATCACCGGCAGA

CTGCAGTCCCTGCAGACCTACGTGACACAGCAGCTGATCAGGGCAGCAGA

GATCAGGGCCTCTGCCAATCTGGCCGCCACAAAGATGAGCGAGTGCGTGC

TGGGACAGTCCAAGAGGGTGGACTTTTGCGGCAAGGGCTATCACCTGATG

AGCTTCCCACAGTCCGCCCCTCACGGAGTGGTGTTTCTGCACGTGACCTA

CGTGCCAGCCCAGGAGAAGAACTTCACCACAGCCCCCGCCATCTGTCACG

ATGGCAAGGCCCACTTTCCTAGGGAGGGCGTGTTCGTGAGCAACGGCACC

CACTGGTTTGTGACACAGCGCAATTTCTACGAGCCACAGATCATCACCAC

AGACAATACCTTCGTGTCCGGCAACTGCGACGTGGTCATCGGCATCGTGA

ACAATACAGTGTATGATCCTCTGCAGCCAGAGCTGGACTCTTTTAAGGAG

GAGCTGGATAAGTACTTCAAGAATCACACCAGCCCCGACGTGGATCTGGG

CGACATCTCTGGCATCAATGCCAGCGTGGTGAACATCCAGAAGGAGATCG

ACAGACTGAACGAGGTGGCCAAGAATCTGAACGAGAGCCTGATCGATCTG

CAGGAGCTGGGCAAGTATGAGCAGTACATCAAGTGGCCCTGGTATATCTG

GCTGGGCTTCATCGCCGGCCTGATCGCCATCGTGATGGTGACCATCATGC

TGTGCTGTATGACAAGCTGCTGTTCCTGCCTGAAGGGCTGCTGTTCTTGT

GGCAGCTGCTGTAAGTTTGATGAGGACGATTCCGAGCCTGTGCTGAAGGG

CGTGAAGCTGCACTACACCTAA.
```

Construction of Ad35 vector for S protein expression pAd35-NB2:

With NB1 and NB2 as templates, respectively, PCR amplification was carried out by using NB1-F and NB1-R as primers to obtain an NB1 fragment and by using NB2-F and NB2-R as primers to obtain an NB2 fragment; furthermore, with CMV-R and BGH-F as primers, respectively, and pGA351-EGFP plasmid as a template, the vector plasmid backbone pGA351 was subjected to PCR amplification and then to in vitro two-fragment recombination with the NB1 and NB2 fragments, respectively, using a homologous recombinase (Exnase) to obtain pGA351-NB1 and pGA351-NB2. The pGA351-NB2 was linearized using Bstzl7I and SgarAI, and was subjected to homologous recombination with pAd35ΔE1ΔE3 (i.e., Ad35 empty vector), which was digested to delete the unique restriction site in the E1 region and linearized, by using competent BJ5183 to construct a pAd35-NB2 vaccine vector.

Primer sequence for amplifying NB1:

```
NB1-F:
                                          (SEQ ID NO.: 2)
GCGTTTAAACTTAAGCTTGGTACCGAGCTCGGATCCGCCACCATGTTTGT
TTTTCTTGT

NB1-R:
                                          (SEQ ID NO.: 3)
AGAATAGGGCCCTCTAGACTAGTTTATGTGTAATGTAATTTG
```

Primer sequence for amplifying NB2:

```
NB2-F:
                                          (SEQ ID NO.: 4)
GCGTTTAAACTTAAGCTTGGTACCGAGCTCGGATCCGCCACCATGTTCGT
GTTTCTGGT

NB2-R:
                                          (SEQ ID NO.: 5)
AGAATAGGGCCCTCTAGACTAGTTTATCAGGTGTAGTGCAGCTTC
```

Primer sequence for amplifying pGA351:

```
BGH-F:
                                          (SEQ ID NO.: 6)
TCTAGAGGGCCCTATTCTATAGTGTC

CMV-R:
                                          (SEQ ID NO.: 7)
GGATCCGAGCTCGGTACCAAGCTTAAGTTTAAACGCTAGAGTCCGG
```

PCR conditions: 95° C., 3 min; 95° C., 30 s; 60° C., 30 s; 72° C., 2 min; cycles 30; 72° C., 5 min.

Rescue and production of Ad35-NB2 vector

1) According to a conventional method, pAd35-NB2 was linearized with AsiSI, recovered by means of precipitation in ethanol, and transfected into 293 cells with cationic liposome transfection method;
2) 8 hours after transfection, 2 ml of a DMEM medium containing 5% fetal bovine serum was added, incubated for 7-10 days, and cytopathic effect observation was carried out;
3) after the cytopathic effect was observed, the cells and culture supernatant were collected, freeze-thawed for three times in a water bath at 37° C. and liquid nitrogen, and centrifugated to remove cell debris, and then a 10 cm dish was infected with the supernatant;
4) after 2 or 3 days, the cells and culture supernatant were collected, freeze-thawed for 3 times, centrifugated to remove cell debris, and then 3-5 15 cm dishes were infected with the supernatant;
5) after 2 or 3 days, the cells were collected, freeze-thawed for 3 times, and centrifugated t to remove cell debris;
6) 30 15 cm dishes were infected with the supernatant; after 2 or 3 days, the cells were collected, freeze-thawed for 3 times, and centrifugated to remove cell debris;
7) the supernatant was added to a cesium chloride density gradient centrifuge tube, and centrifuged at 4° C., 40000 rpm, for 4 hours, and a virus band was pipetted out, desalted, and subpackaged; and
8) the virion titer was determined by means of OD260 absorbance, with the calculation formula being: virus concentration =OD260×dilution multiplex36/genome length (Kb), and the virus stock solution was cryopreserved at −80° C.

Detection of Spike gene expression:

According to a conventional method, 2.5 μg of pGA351-NB1 and pGA351-NB2 were respectively transfected into A549 cells using a cationic liposome, and after 48 hours, the cells were collected. The A549 cells were infected with Ad35-NB2 virus, and after 36 h, the cells were collected. The four samples mentioned above were treated with the conventional Western Blot method, and were detected for the protein (FIG. 1).

Figure 1:
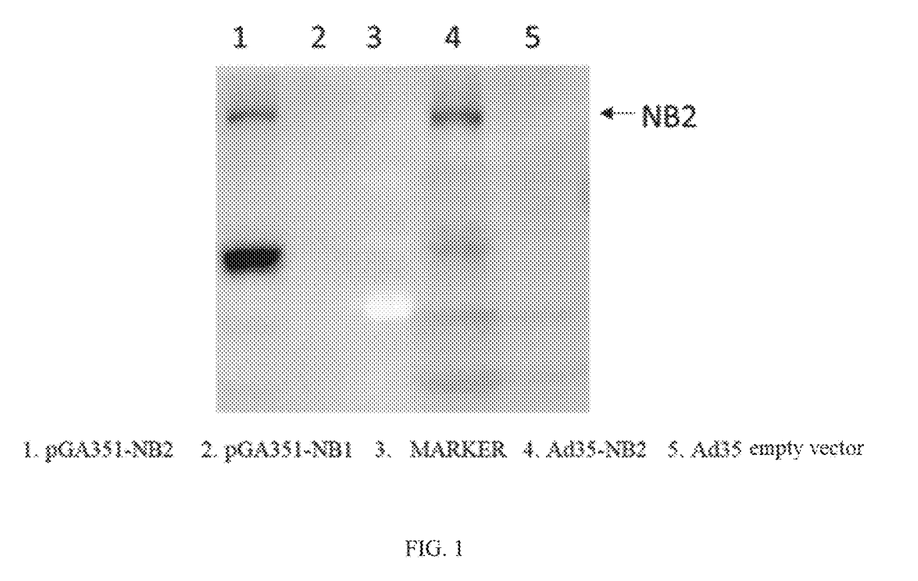
FIG. 1 shows the detection results of the expression of S protein.

It could be seen from FIG. 1 that no S protein expression was detected in the pGA351-NB1 sample, while the S protein expression could be observed in the codon-optimized pGA351-NB2 and vaccine candidate strain Ad35-NB2 samples, indicating that the NB2 sequence has unexpected effects.

Immunogenicity evaluation:

Macaque monkeys were obtained from Guangdong Landau Biotechnology Co. Ltd. The vaccinated macaque monkeys were 2 or 3 years old. The macaque monkeys were randomly divided into 3 groups, with 2 monkeys in each experimental group and 4 monkeys in a control group, specifically as shown in the following table:

| Group No. | Macaque monkey | Sex | Immunization dose/mode |
|---|---|---|---|
| 1 | 170060 | Female | Ad35-NB2 (1 × $10^{11}$ vp) |
| | 170040 | Female | Intramuscular (I.M.) injection |
| 2 | 170025 | Male | Ad35-NB2 (1 × $10^{11}$ vp) |
| | 170051 | Male | intranasal (I.N.) immunization |
| 3 | 180026 | Female | — |
| | 180024 | Female | |
| | 180023 | Male | |
| | 180039 | Male | |

Macaque monkeys were immunized with the vaccine prepared from the Ad35-NB2 virus strain, blood was taken at days 14 and 18, respectively, after immunization, so as to determine the antibody binding titer by using an ELISA method. The peripheral blood was separated and detected for a cellular immune response by using the ELISpot method.

Experimental Results:

(1) Binding Antibodies

Figure 2:
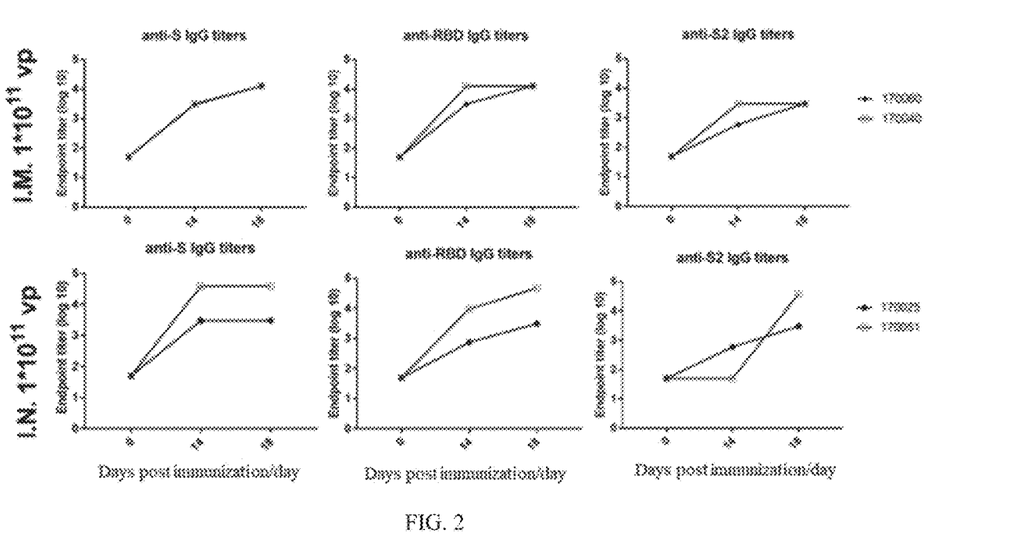
FIG. 2 shows the detection results of binding antibodies in the sera of macaque monkeys at different times after immunization.

At days 14 and 18 after vaccination through intramuscular injection, significant presence of S-specific IgG and RBD-specific IgG could be detected in the sera of all the macaque monkeys intramuscularly injected with 1×$10^{11}$ VP, and among the two macaque monkeys in the immunization group, significant presence of anti-S2 IgG titers was detected in one macaque monkey (FIG. 2).

At day 14 after intranasal immunization n vaccination, significant presence of S-specific IgG and RBD-specific IgG could be detected in the sera of all the macaque monkeys vaccinated with 1×$10^{11}$ VP, and anti-S2 IgG titers could also be detected, but was relatively weak (FIG. 2).

The difference between the antibody titers induced by intramuscular injection immunization and intranasal immunization was small.

(2) Cellular Immunity

In order to determine if the Ad35-NB2 could also induce a cellular immune response in non-human primates (NHPs), the inventors detected the response of S-specific IFN-γ secreting cells from peripheral blood mononuclear cells (PBMCs) to S1 and S2 peptide libraries.

Figure 3:
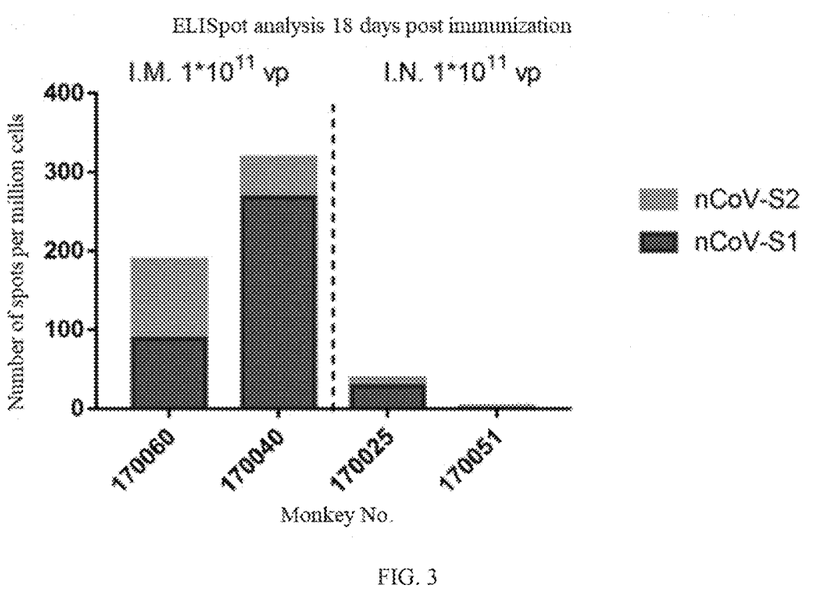
FIG. 3 shows the results of an ELISpot assay on the peripheral blood cells (PBMCs) of macaque monkey 18 days after immunization.

The results showed that:
1) At day 18 after intramuscular injection vaccination, all the macaque monkeys intramuscularly injected with 1×$10^{11}$ VP had cellular immune responses to the S1 and S2 peptide libraries (FIG. 3).
2) At day 18 after intranasal immunization vaccination, among the two vaccinated macaque monkeys, one macaque monkey had a weak cellular immune response to the S1 peptide library, and neither of them had an obvious response to the S2 peptide library at day 18 (FIG. 3).

Therefore, in the macaque monkeys, the cellular immune response was mainly directed at the S1 region. These results indicated that immunization through intramuscular injection could cause a systemic cellular immune response to the S protein, especially to the S1 region, while the systemic cellular immune response caused by the mucosal vaccination of the vaccine was relatively weak.

The above experimental results showed that the vaccine could stimulate macaque monkeys to produce cellular immunity, which could further improve the protection of the body.

The invention claimed is:

1. An immunogenic composition of Ad35-vector for inducing an anti-SARS-COV-2 immune response, comprising an Ad35 vector, wherein the Ad35 vector encodes the optimized nucleic acid sequence of SEQ ID NO: 1.

2. The Ad35-vectored immunogenic composition of claim 1, wherein the Ad35 vector is a replication-defective Ad35 vector.

3. The Ad35-vectored immunogenic composition of claim 2, wherein the replication-defective Ad35 vector is a replication-defective Ad35 vector with genes in E1 and E3 regions deleted.

4. The Ad35-vectored immunogenic composition of claim 1, wherein the Ad35 vector has an element for regulating the expression of the nucleic acid sequence shown in SEQ ID NO: 1.

5. The Ad35-vectored immunogenic composition of claim 1, wherein the transcription direction of the nucleic acid sequence shown in SEQ ID NO: 1 is opposite to the transcription direction of the other genes of the Ad35 vector.

6. The Ad35-vectored immunogenic composition of claim 1, wherein the nucleic acid sequence of SEQ ID NO: 1 can be expressed as the spike or S protein in a human-derived cell or the human body.

7. The Ad35-vectored immunogenic composition of claim 6, wherein the spike or S protein is capable of, in the human body: inducing an immune response: or generating a biological reporter molecule: or generating a trace molecule for detection; or regulating a gene function; or acting as a therapeutic molecule.

8. The Ad35-vectored immunogenic composition of claim 1, wherein the vaccine further comprises at least one selected from the group consisting of pharmaceutically acceptable adjuvant, carrier, diluent or excipient.

9. The Ad35-vectored immunogenic composition of claim 1, wherein the vaccine further comprises at least one drug that has a therapeutic effect on COVID-19.

10. The Ad35-vectored immunogenic composition of claim 2, wherein the Ad35 vector has an element for regulating the expression of the nucleic acid sequence shown in SEQ ID NO: 1.

11. The Ad35-vectored immunogenic composition of claim 3, wherein the Ad35 vector has an element for regulating the expression of the nucleic acid sequence shown in SEQ ID NO: 1.

12. The Ad35-vectored immunogenic composition of claim 2, wherein the transcription direction of the nucleic acid sequence shown in SEQ ID NO: 1 is opposite to the transcription direction of the other genes of the Ad35 vector.

13. The Ad35-vectored immunogenic composition of claim 3, wherein the transcription direction of the nucleic acid sequence shown in SEQ ID NO: 1 is opposite to the transcription direction of the other genes of the Ad35 vector.

14. The Ad35-vectored immunogenic composition of claim 2, wherein the nucleic acid sequence can be expressed as a protein in a human-derived cell or the human body.

15. The Ad35-vectored immunogenic composition of claim 3, wherein the nucleic acid sequence can be expressed as a protein in a human-derived cell or the human body.

16. The Ad35-vectored immunogenic composition of claim 2, wherein the immunogenic composition further comprises at least one selected from the group consisting of pharmaceutically acceptable adjuvant, carrier, diluent or excipient.

17. The Ad35-vectored immunogenic composition of claim 3, wherein the immunogenic composition further comprises at least one selected from the group consisting of pharmaceutically acceptable adjuvant, carrier, diluent or excipient.

18. The Ad35-vectored immunogenic composition of claim 2, wherein the immunogenic composition further comprises at least one drug that has a therapeutic effect on COVID-19.

19. The Ad35-vectored immunogenic composition of claim 3, wherein the immunogenic composition further comprises at least one drug that has a therapeutic effect on COVID-19.

* * * * *